(12) United States Patent
Telschow et al.

(10) Patent No.: US 6,486,962 B1
(45) Date of Patent: *Nov. 26, 2002

(54) METHOD AND APPARATUS FOR ASSESSING MATERIAL PROPERTIES OF SHEET-LIKE MATERIALS

(75) Inventors: Kenneth L. Telschow, Idaho Falls, ID (US); Vance A. Deason, Idaho Falls, ID (US)

(73) Assignee: Bechtel Bwxt Idaho, LLC, Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/393,854

(22) Filed: Sep. 9, 1999

Related U.S. Application Data (63) Continuation-in-part of application No. 09/112,075, filed on Jul. 8, 1998.
(60) Provisional application No. 60/099,631, filed on Sep. 9, 1998.

(51) Int. Cl.[7] .................................................. G01B 9/02
(52) U.S. Cl. ......................... 356/503; 356/502; 356/499
(58) Field of Search ................................. 356/499, 502, 356/432 T, 512, 503

(56) References Cited

U.S. PATENT DOCUMENTS 6,175,411 B1 * 1/2001 Telschow et al. ........... 356/503

OTHER PUBLICATIONS

Telschow, K. L., et al, "Material Property Measurement of Metallic Parts Using INEEL Laser Ultrasonic Camera"; Proceedings of the 38th Conference of Metallurgiest (COM) 29th annual Hydrometallurgical Meeting, Advanced Sensors for Metals Processing, Quebec, Canada, Aug. 22–26, 1999, pp. 1–11.

Telschow, K. L., et al, "INEEL Laser Ultrasonic Measurements on Paper"; INEEL/EXT–98–00920, Jan. 1999.

* cited by examiner

Primary Examiner—Frank G. Font
Assistant Examiner—Andrew H. Lee
(74) Attorney, Agent, or Firm—Dahl & Osterloth LLP (57) ABSTRACT

Apparatus for producing an indication of a material property of a sheet-like material according to the present invention may comprise an excitation source for vibrating the sheet-like material to produce at least one traveling wave therein. A light source configured to produce an object wavefront and a reference wavefront directs the object wavefront toward the sheet-like material to produce a modulated object wavefront. A modulator operatively associated with the reference wavefront modulates the reference wavefront in synchronization with the traveling wave on the sheet-like material to produce a modulated reference wavefront. A sensing medium positioned to receive the modulated object wavefront and the modulated reference wavefront produces an image of the traveling wave in the sheet-like material, the image of the anti-symmetric traveling wave being related to a displacement amplitude of the anti-symmetric traveling wave over a two-dimensional area of the vibrating sheet-like material. A detector detects the image of the traveling wave in the sheet-like material.

30 Claims, 3 Drawing Sheets

METHOD AND APPARATUS FOR ASSESSING MATERIAL PROPERTIES OF SHEET-LIKE MATERIALS

CROSS REFERENCE TO RELATED APPLICATION

This is a continuation in part of co-pending U.S. application, Ser. No. 09/112,075, filed on Jul. 8, 1998, which is incorporated herein by reference for all that it discloses.

REFERENCE TO CO-PENDING PROVISIONAL APPLICATION

Applicants hereby claim the benefit of an earlier filed co-pending provisional application, Application No. 60/099,631, filed on Sep. 9, 1998, which is incorporated wherein by reference for all that it discloses.

CONTRACTUAL ORIGIN OF THE INVENTION

The United States Government has rights in this invention pursuant to Contract No. DE-AC07-94ID 13223 between the U.S. Department of Energy and Lockheed Martin Idaho Technologies Company.

FIELD OF INVENTION

This invention relates generally to methods and apparatus for assessing material properties and more specifically to methods and apparatus for assessing material properties of paper and other sheet-like materials.

BACKGROUND OF THE INVENTION

The paper industry has for several years utilized various types of ultrasonic testing methods in order to evaluate certain material properties of paper, such as elastic properties (e.g., stiffness). Depending on the intended application, it may be desirable for the elastic properties (e.g., stiffness) of the paper to be substantially the same in all directions, in which case the elastic properties are said to be isotropic. Alternatively, the elastic properties of the paper may vary with direction, in which case the elastic properties are referred to as being anisotropic. One technique for measuring the elastic properties of paper involves measuring the speed of an elastic wave as it moves between 2 points on the material. Since the speed of an elastic wave in paper is related to the elastic properties (e.g., stiffness) of the paper, measurement of the time it takes for an elastic wave to travel between the two points on the paper can be used to ascertain the elastic properties of the paper along the line defined by the two points. An assessment of the elastic properties of the paper along several directions may be ascertained by performing the elastic wave measurement technique between several pairs of points at several different angles. For example, it is common to perform the elastic wave measurement technique in the so-called "machine direction" as well as the perpendicular or "cross direction" in order to assess the elastic properties of the paper in these two directions.

An example of a method and apparatus for performing the above-referenced measurement technique involves the use of a contact-type piezoelectric emitter and a detector. The piezoelectric emitter may be placed in contact with the paper at a central location. The detector may then be placed at one of a plurality of discrete locations along a circle surrounding the emitter. Measurements may then be taken at each discrete location around the emitter by using the detector to calculate the time it takes a given elastic wave to travel from the emitter to the detector. The travel time may then be used to determine the velocity of the elastic wave along that particular direction. Thereafter, the velocity differences along specific directions may be used to assess the elastic properties of the paper along several different directions.

While the foregoing method for measuring the elastic properties of paper is effective from a functional standpoint and is widely used, it is not without its drawbacks. For example, such a point measurement technique is slow and difficult to automate because the detector must be positioned or moved to each of a number of discrete locations about the emitter in order to detect the velocity of the elastic wave along all directions of the paper sample being tested. Another disadvantage associated with the foregoing measurement technique is that it is not particularly well-suited for real time or "on the fly" measurements. Consequently, to date, such point contacting methods have not been successfully implemented on a moving paper stream, such as may be found in a paper manufacturing plant. Instead, a sample of paper must be removed from the paper stream and separately analyzed. Of course, if the elastic properties of the paper in any direction are found to be non-compliant with specifications, a substantial portion of the paper from the sample lot may need to be separately analyzed to determine the extent of the non-compliance. In extreme cases, the entire lot may need to be scrapped.

Consequently, a need exists for a method and apparatus for more readily determining certain material properties of paper and other sheet-like materials that does not suffer from the shortcomings of prior art methods and apparatus. Additional advantages could be realized if such a new method and apparatus could be more readily implemented in a production environment to provide a real time assessment of material properties (e.g., stiffness), thereby making it easier to provide "on-the-fly" measurement and/or adjustment of the tested properties or parameters.

SUMMARY OF THE INVENTION

Apparatus for producing an indication of a material property of a sheet-like material according to the present invention may comprise an excitation source for vibrating the sheet-like material to produce at least one traveling wave therein. A light source configured to produce an object wavefront and a reference wavefront directs the object wavefront toward the sheet material to produce a modulated object wavefront. A modulator operatively associated with the reference wavefront modulates the reference wavefront in synchronization with a traveling wave on the sheet-like material to produce a modulated reference wavefront. A sensing medium positioned to receive the modulated object wavefront and the modulated reference wavefront produces an image of the traveling wave in the sheet-like material, the image of the traveling wave being related to a displacement amplitude of the traveling wave over a two-dimensional area of the vibrating sheet-like material. A detector detects the image of the traveling wave in the sheet-like material.

Also disclosed is a method for assessing a material property of a sheet like material which may comprise the steps of: vibrating the sheet-like material to produce at least one traveling wave therein; directing an object wavefront toward the vibrating sheet-like material so that the object wavefront is modulated by the vibrating sheet-like material to produce a modulated object wavefront; modulating a reference wavefront in synchronization with the vibrating sheet-like material to produce a modulated reference wavefront so that a difference frequency between the modulated object wavefront and the modulated reference wavefront is within a response range of the sensing medium; combining the modulated object wavefront and the modulated reference wavefront within the sensing medium to produce an image of the traveling wave in the vibrating sheet-like material, the image of the traveling wave being related to a displacement amplitude of the traveling wave over a two-dimensional area of the vibrating sheet-like material; detecting an image of the traveling wave in the vibrating sheet material; and assessing the material property of the vibrating sheet material based on the detected image of the traveling wave.

BRIEF DESCRIPTION OF THE DRAWING

Illustrative and presently preferred embodiments of the invention are shown in the accompanying drawing in which.

DETAILED DESCRIPTION OF THE INVENTION

Figure 1:
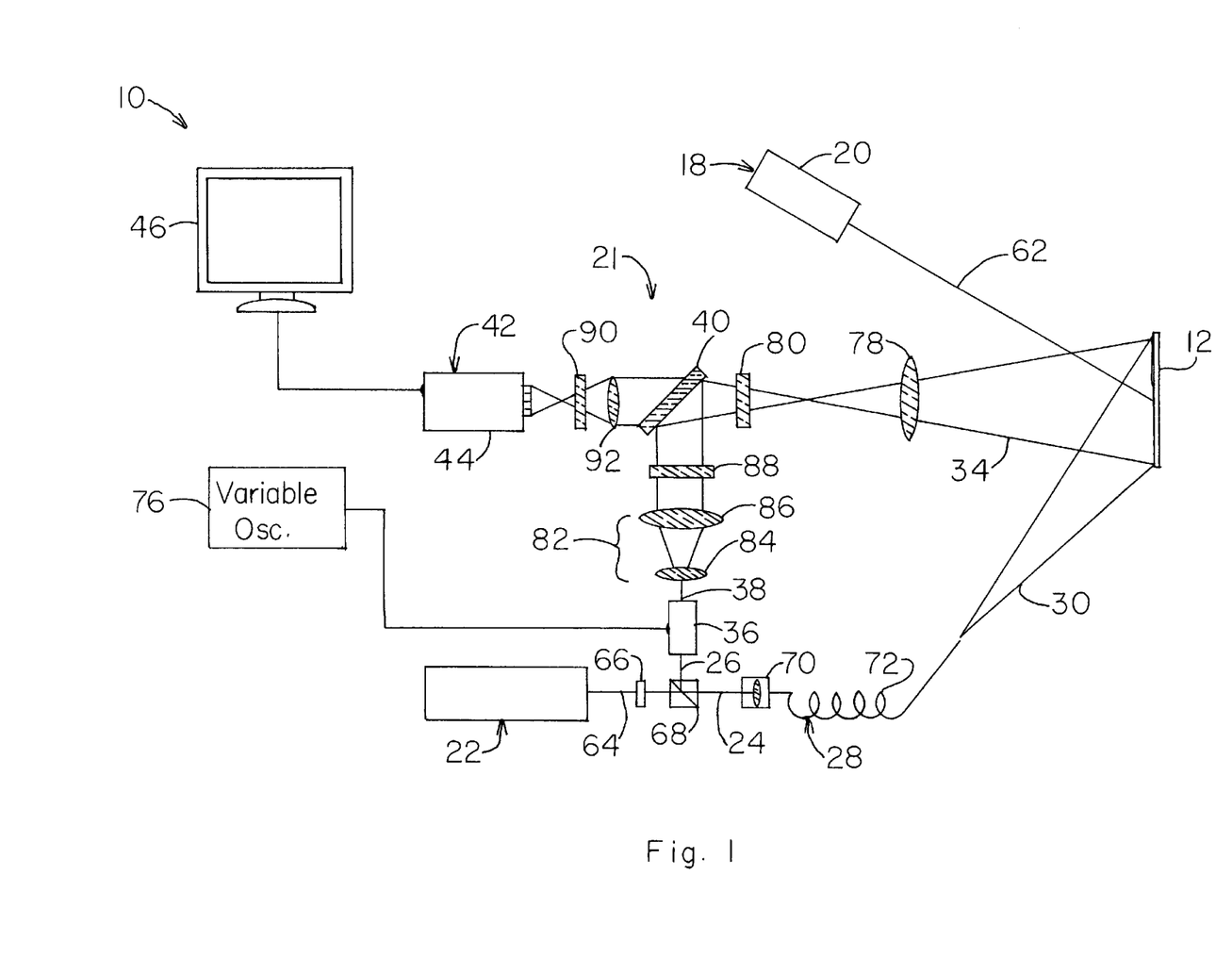
FIG. 1 is a schematic representation of apparatus for assessing a material property of a sheet-like material according to one embodiment of the present invention.

Apparatus 10 for assessing a material property of a sheet-like material, such as a paper sample 12, is best seen in FIG. 1 and produces an image 14 (illustrated schematically in FIG. 2) of a traveling elastic wave 16 in the paper sample 12. As will be described in greater detail below, the image 14 of the traveling elastic wave 16 is reconstructed from a hologram (not shown) produced by a sensing medium 40 associated with the apparatus 10. The shape and orientation of the traveling wave 16 contained in the reconstructed image 14 may be used to ascertain certain material properties (e.g., elastic properties) of the paper sample 12. Moreover, since the image 14 of the traveling wave comprises a two dimensional image of motion over an extended area, the present invention may be used to readily ascertain material properties along all planar directions simultaneously.

Before proceeding with the description, it should be noted that the terms "sheet-like material" and "sheet material" as used herein refer to materials having dimensions in either the length or width directions, or both, that are much greater than the dimension of the material in the thickness direction. Examples of sheet-like materials include, but are not limited to, paper, vellum, plastic films, thin metallic sheet materials, and thin metallic foils.

Continuing now with the description, the apparatus 10 for assessing a material property of a sheet-like material, such as sheet of paper 12, may comprise an excitation source 18, such as a laser 20, for vibrating the paper sample 12 to produce one or more traveling elastic waves (e.g., traveling wave 16, FIG. 2) in the paper sample 12. The traveling waves (e.g., traveling wave 16) induced in the paper sample 12 by the excitation source 18 are detected and imaged with the aid of a photorefractive imaging system 21. In the embodiment shown and described herein, the photorefractive imaging system 21 may comprise a light source assembly 22 which produces two mutually coherent light beams or wavefronts: An object beam or wavefront 24 and a reference beam or wavefront 26. An optical beam confining and directing device 28 (e.g., a fiber optic cable 72) operatively associated with the object beam 24 spreads and directs the object beam 24 onto the vibrating paper sample 12 as an expanded object beam 30. The expanded object beam 30 illuminates a two-dimensional area or region 32 (FIG. 2) on the paper sample 12. Thereafter, the vibrating paper sample 12 modulates the phase of the expanded object wavefront or beam 30 to form a phase modulated object wavefront or beam 34.

The reference beam or wavefront 26 produced by the light source assembly 22 is directed through a beam modulator 36 to produce a modulated reference beam 38. As will be explained in greater detail below, the beam modulator 36 modulates the phase of the reference beam 26 at a frequency that is slightly different than the frequency of the traveling wave 16 sought to be detected on the paper sample 12. The modulated reference beam or wavefront 38 is then directed toward a sensing medium 40 wherein the modulated reference beam 38 is combined with the modulated object beam 24 reflected by the vibrating paper sample 12.

In the embodiment shown and described herein, the sensing medium 40 may comprise a photorefractive material, such as a bismuth silicon oxide crystal. As used herein, the term "photorefractive" refers to those materials wherein the space charge electrical grating can be either in-phase or out-of-phase with the optical interference pattern. When the modulated object and reference beams 34 and 38 are combined within the photorefractive sensing medium 40, they create a space charge field (not shown) having a magnitude that is directly proportional to the vibrational displacement (i.e., amplitude) of the traveling waves (e.g., traveling wave 16) in the paper sample 12 and that is a cosine function of the vibration phase of the traveling wave 16 (for small amplitudes). The space charge field modulates the local refractive index of the sensing medium 40 (via the electro-optical effect), creating a diffraction grating within the sensing medium 40 that embodies the desired low-frequency phase information. The result is the formation of a hologram (not shown) which may be used to reconstruct an image 14 (illustrated generally in FIG. 2) of the elastic wave displacement distribution on the paper sample 12. The intensity variations of the reconstructed image 14 are proportional to the phase difference between the modulated object and reference beams 34 and 38, respectively. The reading-out of the halogram to reconstruct the image of the traveling ultrasonic wave can be performed by the same detection laser beam as indicated in FIG. 1 for the out-of-phase gratings. For the in-phase gratings, a separate independent laser beam at a different wavelength may be used by employing the appropriate Bragg angle to reconstruct the image of the ultrasonic wave.

As will be described in greater detail below, the photorefractive material comprising the sensing medium 40 has a limited response time, i.e., cut-off frequency. Consequently, the photorefractive sensing medium 40 will not record interference patterns having frequencies above the cut-off frequency of the sensing medium 40. Since the reference beam 26 is modulated at a frequency that is very close to, but not the same as, the frequency of the traveling wave 16 in the paper sample 12, and since the difference between the frequencies is less than the cut-off frequency of the photorefractive sensing medium 40, the resulting image 14 (FIG. 2) reconstructed from the hologram (not shown) produced by the photorefractive sensing medium 40 moves at a speed that is related to the frequency difference between the modulated object beam 34 and the modulated reference beam 38. Moreover, since the cut-off frequency of the photorefractive sensing medium 40 is generally lower than the elastic wave frequency, the photorefractive sensing medium 40 will not record disturbances and waves if the frequencies of the disturbances and waves are such that the differences between those frequencies and the frequency of the modulated reference beam are greater than the cut-off frequency of the photorefractive sensing medium 40. Stated simply, the photorefractive sensing medium 40 functions as a mixer and as a low pass filter, recording only those interference patterns having frequencies less than the cut-off frequency of the photorefractive sensing medium 40.

The image 14 (FIG. 2) reconstructed from the hologram (not shown) produced within the photorefractive sensing medium 40 may be detected by suitable array (i.e., two-dimensional) detector 42, such as a video camera 44. In an alternative embodiment, the reconstructed image 14 may be directly observed by the human eye via an eyepiece (not shown) or other such device. If a video camera 44 is used to detect the reconstructed image 14, the video camera 44 may be connected to a display device 46, such as a CRT or LCD panel, suitable for displaying the reconstructed image 14. Alternatively, the image 14 captured by the video camera 44 may be recorded on a suitable medium (e.g., video tape) for later playback and/or analysis.

As mentioned above, the excitation source 18 may be used to induce a series of vibrations or more specifically, traveling elastic waves, in the paper sample 12. If the wavelengths of the elastic waves are greater than the thickness of the material (e.g., paper 12) or other sheet-like material comprising the sample, two predominant wave modes will be created: An anti-symmetric ($A_n$) or flexural mode, and a symmetric ($S_n$) or thickness mode, where n=0,1,2, . . . As used herein, the subscript "n" is used to denote the order of the wave, with n=0 corresponding to the lowest (i.e., zeroth) order mode. Elastic waves having the zeroth order mode (i.e., n=0) are generally the easiest to generate and detect and are therefore generally used for diagnostic measurements. Accordingly, the following description will refer to waves of the zeroth order.

While the velocity of a symmetric or $S_0$ mode wave is generally faster than that of an anti-symmetric or $A_0$ mode wave, the amplitude of the $S_0$ mode wave is usually smaller for single sided excitation, i.e., where the sheet like material is excited or vibrated from a single side of the sheet. Also, at low frequencies the symmetric or $S_0$ mode wave is also relatively non-dispersive (i.e., not subject to dispersion effects) compared with the $A_0$ mode wave, which is generally highly susceptible to dispersion effects.

Until this invention, the foregoing characteristics of the $A_0$ and $S_0$ wave modes have placed significant limitations on the methods and apparatus that could be used effectively to measure the traveling waves produced in such a paper sample. For example, while the $A_0$ waves are generally easier to detect and measure due to their slower speeds and larger amplitudes, their susceptibility to dispersion effects has made them generally unsuitable for use where the sample is excited by a single impulse or by a series of impulses (referred to herein as pulse-type excitation). As is well-known, such pulse type excitation of a system generally results in the production of waves or vibrations comprising a broad range of frequencies. Complex signal processing procedures are typically required in order to determine the elastic properties of the material from such dispersive modes. However, at low frequencies, the $S_0$ mode is not dispersive, thereby allowing a simple measure of the wave speed from the time it takes the wave to traverse a known distance. Consequently, prior art systems rely on the detection and measurement of traveling waves of the symmetric ($S_0$) mode produced by pulse-type excitation sources.

In contrast to the prior art, the method and apparatus of the present invention is capable of imaging any of the plate or surface elastic wave modes and can be readily used to detect and measure the anti-symmetric or $A_0$ mode traveling waves, regardless of whether the paper sample is vibrated by continuous, "tone burst," amplitude modulated, or pulse-type excitation sources. The extreme dispersion that is associated with the $A_0$ mode wave is effectively accounted for out by the frequency selectivity that is associated with the photorefractive imaging system 21. That is, the photorefractive imaging system 21 allows a traveling wave of a specific frequency to be readily imaged while removing or filtering out images of waves having other frequencies.

Figure 2:
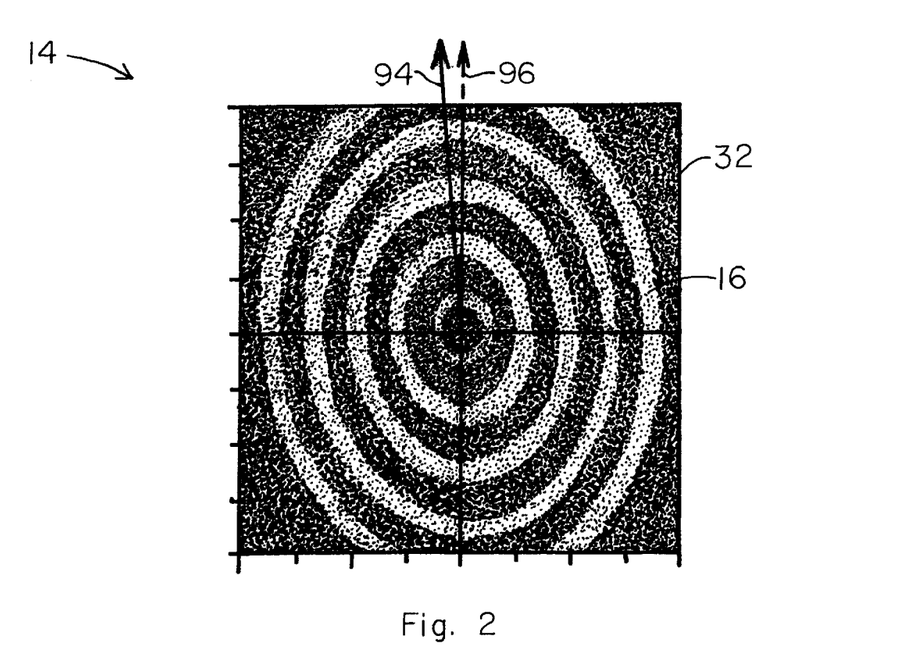
FIG. 2 is a schematic representation of an image of a traveling elastic wave reconstructed from a hologram produced by optical interference within the photorefractive sensing medium.
Figure 3:
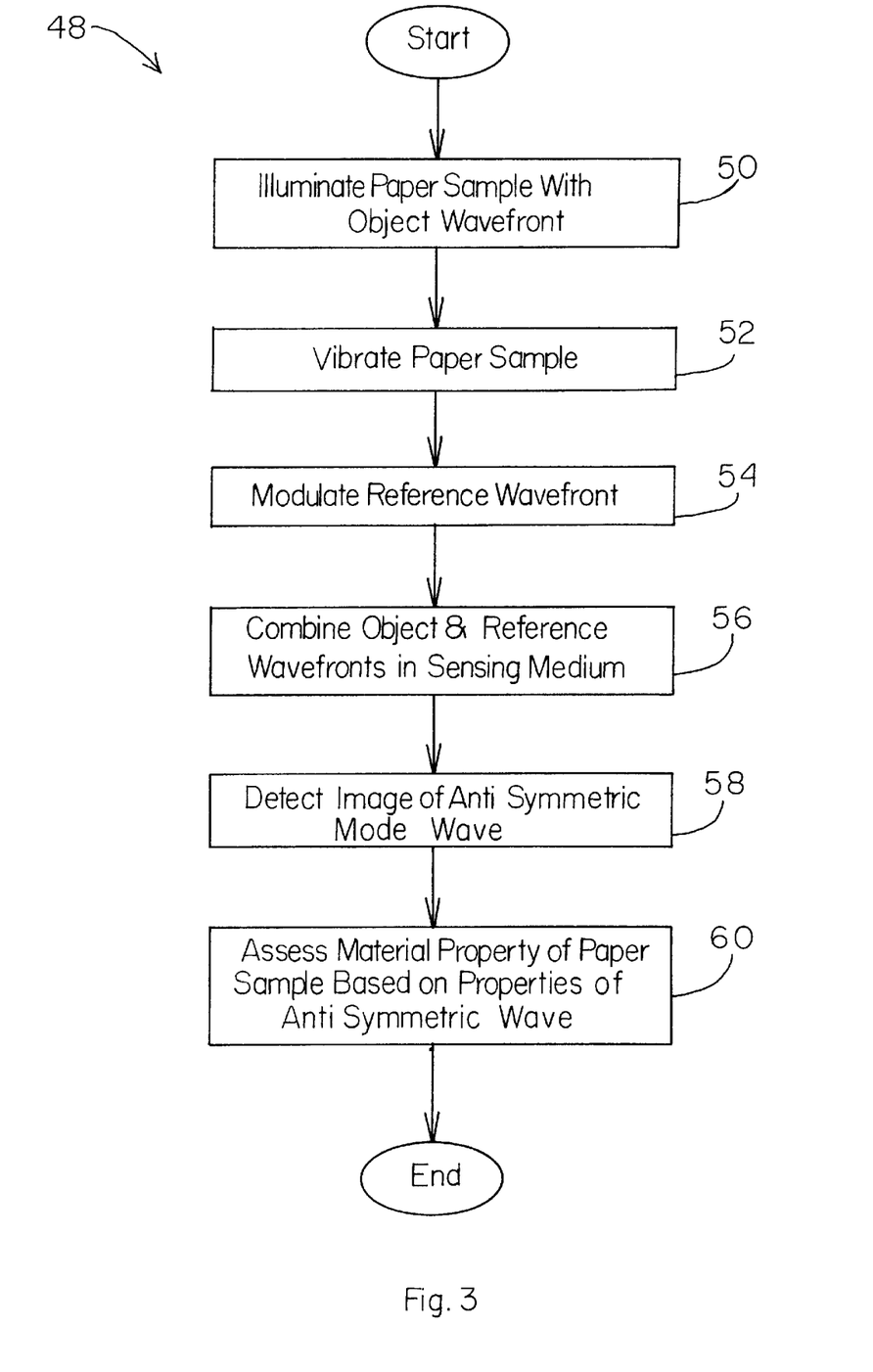
FIG. 3 is a flow chart of a method for assessing a material property of a sheet-like material according to one embodiment of the present invention.

The apparatus 10 for assessing a material property of a paper sample 12 may be operated according to the method 48 illustrated in FIG. 3 in order to assess a material property of the sheet-like material, e.g., paper sample 12. The first step 50 in the method 48 is to illuminate the paper sample 12 with the object beam or wavefront 30. The paper sample 12 may then be vibrated at step 52 to cause the formation of one or more traveling waves (e.g., traveling wave 16) in the paper sample 12. Alternatively, the paper sample 12 may be vibrated before illuminating the paper sample 12 with the object beam 30. That is, step 52 may be performed before step 50. In still another arrangement, the illumination and vibration steps may occur substantially simultaneously. Regardless of the order in which the illumination and vibration steps 50 and 52 are performed, the traveling wave (e.g., traveling wave 16) produced in the paper sample 12 modulates the phase of the expanded object beam 30 to form a modulated object beam 34. See FIG. 1. The next step in the method 48 is to modulate the phase of the reference beam or wavefront 26 to produce a modulated reference beam 38. As was briefly mentioned above, the phase of the reference beam 26 is modulated at a frequency that is slightly different than the frequency of the traveling wave that is to be detected. The modulated object beam 34 and modulated reference beam 38 are then combined within the photorefractive sensing medium 40 at step 56 which produces a hologram (not shown) from which may be reconstructed an image 14 (FIG. 2) of the traveling wave 16. In the embodiment shown and described herein, it is preferred that the traveling wave 16 comprise an anti-symmetric or $A_0$ mode wave. Alternatively, other wave modes may also be imaged, as will be described in greater detail below. The reconstructed image 14 of the $A_0$ mode wave 16 is then detected at step 58 and analyzed at step 60 to assess a material property of the paper sample 12.

Referring back now to FIG. 2, the anti-symmetric mode traveling waves (e.g., traveling wave 16) that may be detected in step 58 are indicative of certain material properties (e.g., elastic properties) of the paper sample 12. For example, since the velocity of the traveling wave 16 is related to the stiffness of the paper (and on other such elastic properties), the speed of the traveling wave 16 may be used to assess the stiffness of the paper sample 12. Since the reconstructed image 14 is two-dimensional along the height and length of the paper sample 12, the velocity of the traveling waves (e.g., traveling wave 16) may be determined in all directions from a single image.

Figure 4:
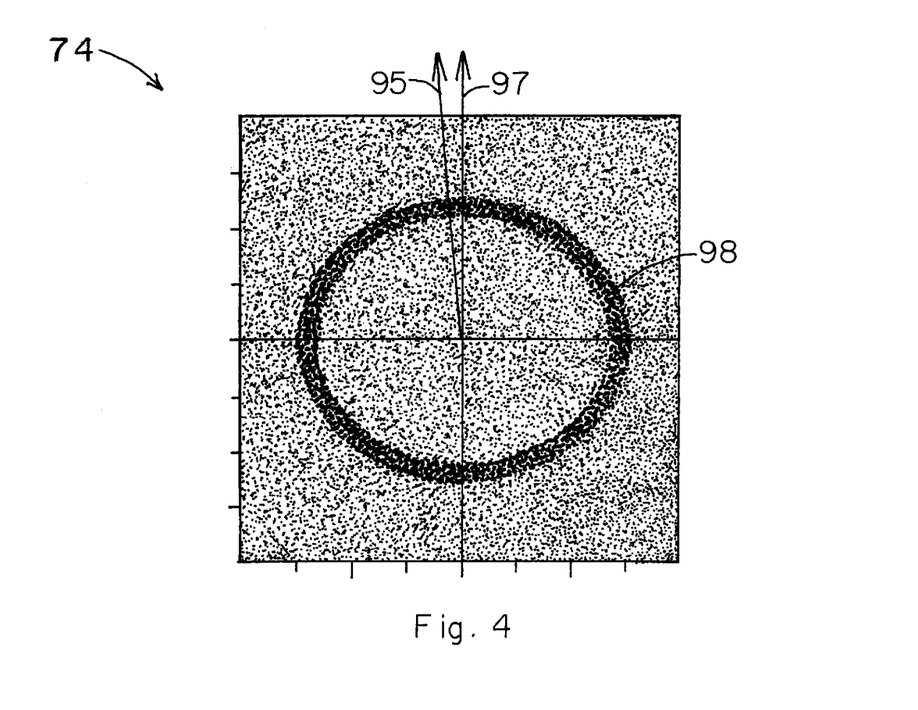
FIG. 4 is a schematic representation of a Fourier transform of the traveling wave illustrated in FIG. 2.

While the velocity of the traveling wave pattern may be determined from the two dimensional image 14 contained within the sensing medium 40 (e.g., by measuring the elastic wavelength from the image 14 and then by multiplying the elastic wavelength by the excitation frequency to obtain the phase velocity of the elastic wave), it is generally more convenient to transform the traveling wave pattern from the spatial domain into the spatial frequency domain. Such a spatial frequency domain representation shows directly the different wavelengths for the wave in different directions. As will be described in greater detail below, any of a wide range of methods well-known in the art, such as Fast Fourier Transform (FFT) techniques, may be used to transform the traveling wave pattern from the spatial domain to the spatial frequency domain. Alternatively, other methods, such as image processing routines and mathematical transforms may also be used. An example of such a transformed traveling wave pattern 74 is illustrated in FIG. 4. The single, ring-like pattern is a measure of wave "slowness" (i.e., the reciprocal of the wave speed) and/or the elastic coefficients for that wave mode in all planar directions. Put in other words, FIG. 4 directly illustrates in two dimensions the anisotropy in the elastic behavior of the material.

A significant advantage associated with the method and apparatus according to the present invention is that it provides a totally non-contacting means for assessing material properties of paper and other like materials. Consequently, the method and apparatus according to the present invention offer the possibility of providing for convenient real-time assessment of material properties in two dimensions. Such real-time assessment of material properties also offers the possibility of providing "on the fly" adjustment of such material properties during production to ensure continuous compliance with parameter limits.

Another advantage of the present invention is that it assesses the desired material properties based on the detection and measurement of anti-symmetric mode waves. Since anti-symmetric mode waves generally travel at slower velocities and have larger amplitudes than symmetric mode waves, anti-symmetric mode waves are generally easier to detect and also generally provide an increased signal to noise ratio over methods and apparatus which detect and measure symmetric mode waves.

Still another advantage associated with the method and apparatus of the present invention is that it allows the sample being measured to be excited with any of a wide range of excitation modes, such as continuous, "tone burst", amplitude modulated, and pulse-type excitation. The ability to utilize any of a wide variety of excitation modes (e.g., "tone burst" or pulse-type excitation) further enhances the ability of the present invention to be used to provide a real time or on the fly assessment of material properties, especially in a dynamic production environment.

Having briefly described one embodiment of the method and apparatus for assessing a material property of a sheet-like material, as well as some of its more significant advantages, the various embodiments of the method and apparatus according to the present invention will now be described in detail. However, before proceeding with the detailed description of the various embodiments, it should be noted that the present invention is shown and described herein as it could be used to determine at least one material property (e.g., paper stiffness) of a particular type of sheet-like material (e.g., paper sample 12). However, the invention could be used to determine other properties (e.g., fiber orientation, material thickness, stress, defects, etc.) for all types of thin, sheet-like materials (e.g., vellum, plastic films, thin metallic foils, etc.), as would be obvious to persons having ordinary skill in the art after having become familiar with the teachings of the present invention. Consequently, the present invention should not be regarded as being limited to the particular materials and material properties shown and described herein.

With the foregoing considerations in mind, one embodiment of an apparatus 10 according to the present invention is shown in FIG. 1 as it could be used to determine a material property (e.g., stiffness) of a paper sample 12. It should be noted that the paper sample 12 may comprise a separate sample of paper produced in a production environment, in which case the analysis provided by means of the method and apparatus of the present invention may be performed on an intermittent or batch type basis. That is, a portion of the paper may be removed from the production line and separately analyzed. Alternatively, the paper sample 12 may comprise a portion or segment of a continuously moving supply of paper produced in a production environment. If so, the analysis provided by means of the method and apparatus of the present invention may be performed "on-the-fly," i.e., during the actual paper production process.

Proceeding now with the description, the apparatus 10 may comprise an excitation source 18 which vibrates the paper sample 12 in order to induce one or more traveling waves (e.g., traveling wave 16, FIG. 2) therein. As was mentioned above, the excitation source 18 may comprise any of a wide range of devices for producing either continuous, "tone burst," amplitude modulated, or pulsed-type excitation of the sample 12, thereby resulting in the formation of one or more traveling waves (e.g., traveling wave 16) in the paper sample 12. By way of example, the excitation source 18 utilized in one preferred embodiment of the present invention may comprise a pulsed laser 20 which produces a high intensity, short duration flash or beam of light 62 which is directed onto the paper sample 12. Depending on the energy delivered by the periodic flash or beam 62, the vibrations in the paper sample 12 may be generated as a result of either thermoelastic expansion (at lower energies) or as a result of ablation (at higher energies). Of the two wave generating modes, the former mode (i.e., thermoelastic expansion) is generally preferred in that it does not damage the paper sample 12. However, the first mode generally produces smaller wave displacements. The particular mode (i.e., thermoelastic expansion or ablation) that may be desired or required in any given application will depend on the type of material being measured as well as on the degree of damage that can be tolerated in the material sample. Therefore, the present invention should not be regarded as limited to either the thermoelastic or ablation modes of excitation.

The excitation laser 20 may comprise any of a wide range of pulsed type laser systems now known in the art or that may be developed in the future. Consequently, the present invention should not be regarded as limited to any particular type of laser. However, by way of example, in one preferred embodiment, the laser 20 may comprise a solid state laser for producing an output beam having a wavelength of about 1064 nanometers (nm), and a pulse duration in the range of about 0.01 microseconds ($\mu$s) to about 10.0 $\mu$s. The energy of each pulse may be in the range of about 0.1 to about 10 millijoules (mJ), with a pulse repetition rate at the desired ultrasonic frequency greater than about 100 Hz. Alternatively, lasers having other wavelengths, operational modes (e.g., continuous, tone burst, amplitude modulated, or pulse) and energies may also be used depending on the requirements of the particular application, as would be obvious to persons having ordinary skill in the art after having become familiar with the teachings of the present invention.

In an alternative embodiment, the excitation source 18 may comprise a contact-type excitation source, such as a piezoelectric transducer (not shown), which may be placed in contact with the paper sample 12 to induce therein vibrations of a suitable frequency. For example, it is generally preferred that the paper sample 12 be vibrated at a frequency or at frequencies in the ultrasonic range (i.e., frequencies in excess of about 100 kHz), although other frequencies may also be used. However, such contact-type excitation sources are not generally preferred in that they limit the environment in which the method and apparatus according to the present invention may be used. That is, such a contact-type excitation source will usually limit practical use of the invention to those situations wherein it is convenient to place the excitation source in physical contact with the paper sample 12. In contrast, the laser type excitation source 18 described above does not require contact with the paper sample 12. Alternatively, the paper source 12 could be vibrated by any of other types of non-contact elastic wave excitation sources, such as electromagnetic acoustic transducers or air-coupled transducers, as would be obvious to persons having ordinary skill in the art after having become familiar with the teachings of the present invention.

The excitation source 18 induces a series of vibrations or more specifically, elastic waves, in the paper sample 12. If the wavelengths of the elastic waves are greater than the thickness of the material (e.g. paper 12) to be measured, two predominant wave modes may be produced: An antisymmetric ($A_0$) or flexural mode, and a symmetric ($S_0$) or thickness mode. As mentioned above, it is generally preferred, but not required, to measure traveling waves of the zeroth mode (i.e., n=0), hence the "0" subscript is used to denote the antisymmetric and symmetric mode waves. While the velocity of a symmetric or $S_0$ mode wave is generally faster than that of an anti-symmetric or $A_0$ mode wave, the amplitude of the $S_0$ mode wave is usually smaller. Also, at low frequencies the symmetric or $S_0$ mode wave is also relatively non-dispersive (i.e., not subject to dispersion effects) compared with the $A_0$ mode wave, which is generally highly susceptible to dispersion effects.

The traveling waves (e.g., traveling wave 16, FIG. 2) induced in the paper sample 12 by the excitation source 18 may be detected and imaged with the aid of a photorefractive imaging system 21. In the embodiment shown and described herein, the photorefractive imaging system 21 may comprise a photorefractive imaging system of the type shown and described in the parent application to this patent application, i.e., U.S. patent application Ser. No. 09/112,075, filed on Jul. 8, 1998, and entitled "Apparatus and Method for Measuring and Imaging Traveling Waves" of Telschow and Deason, which is referred to above and which is incorporated herein by reference. Briefly, the photorefractive imaging system 21 disclosed in that patent application may comprise a light source assembly 22 which produces two mutually coherent light beams or wavefronts: An object beam or wavefront 24 and a reference beam or wavefront 26. The object and reference beams 24 and 26 are preferably derived from a single, coherent source beam 64 produced by the light source assembly 22.

The light source assembly 22 which may be used to generate the single, coherent source beam 64 may comprise any of a wide range of lasers that are now known in the art or that may be developed in the future that would be suitable for producing such a coherent source beam 64. By way of example, in one preferred embodiment of the present invention, the light source 22 may comprise a 200 milliwatt (mw) argon laser capable of producing a coherent source beam having a wavelength of about 514 nanometers (nm). Alternatively, lasers having other output powers and beam wavelengths could also be used.

The source beam 64 produced by the light source assembly 22 (e.g., laser) first may be directed through a quarter wave plate 66 before being directed to abeam splitter 68 which splits the source beam 64 into the object beam 24 and the reference beam 26. Thereafter the object beam 24 may be directed to a beam confining and directing device 28 which directs the object beam 24 onto the vibrating paper sample 12 as an expanded object beam 30. While any of a wide range of components or combinations of components may be used to direct the object beam 24 onto the paper sample 12, in one preferred embodiment, the beam directing device 28 may comprise a beam coupling lens 70 and optic fiber or light pipe assembly 72. Such an arrangement converts the object beam 24 into an expanded, generally cone-shaped beam 30 and allows the expanded beam 30 to be conveniently directed onto the desired portion of the paper sample 12 to illuminate a two-dimensional area or region 32 (FIG. 2) thereof.

The various components described above (e.g., beam splitter 68, coupling lens assembly 70, and optic fiber assembly 72) for producing the expanded object beam 30 and for directing it onto the paper sample 12 may comprise any of a wide range components and devices that are well-known in the art and readily commercially available. Consequently, the particular beam splitter 68, coupling lens assembly 70, and optic fiber assembly 72 which may be utilized in one preferred embodiment of the present invention will not be described in further detail herein.

The vibrating paper sample 12 modulates the phase of the expanded object beam 30 to produce modulated object beam 34. Thereafter, phase modulated object beam 34 is collected by a collection lens 78 which focuses the modulated object beam 34 onto the photorefractive sensing medium 40. A polarizer 80 positioned between the collection lens 78 and the photorefractive sensing medium 40 may comprise a high extinction ratio polarizer to select one polarization component of the modulated object beam 34 for passage onto the photorefractive sensing medium 40.

In an alternative arrangement, the expanded object beam 30 may be transmitted through the paper sample 12, instead of being reflected by the paper sample 12. If the expanded object beam 30 is transmitted through the vibrating paper sample 12, the variations in density and thickness of the vibrating paper sample 12 modulate the phase of the expanded object beam to form a phase modulated object beam. Thereafter, the phase modulated object beam may be recombined with the modulated reference beam 38 in the manner shown and described herein.

The reference beam 26 emerging from the beam splitter 68 is directed through a beam modulator 36 which modulates the phase of the reference beam 26 to produce a modulated reference beam 38. In the embodiment shown and described herein, the beam modulator 36 comprises an electro-optic modulator of the type well-known in the art for modulating the phase of the reference beam 26. A variable oscillator 76 of the type that is also well-known in the art and operatively associated with the beam modulator 36 allows the beam modulator 36 to modulate the phase of the reference beam 26 at a frequency that is slightly different than the frequency of the phase modulation of the modulated object beam 34. For example, and as will be described in greater detail below, the variable oscillator 76 may be adjusted so that the beam modulator 36 modulates the phase of the reference beam at a frequency differing from the object wave modulation frequency by about 25 Hz. Alternatively, other frequencies may also be used as would be obvious to persons having ordinary skill in the art after having become familiar with the teachings of the present invention.

After being modulated by beam modulator 36, the modulated reference beam 38 may be expanded by a suitable beam expander assembly 82 which, in one preferred embodiment may comprise a pair of lenses 84 and 86. A polarizer 88 positioned between the beam expander assembly 82 and the photorefractive sensing medium 40 selects (i.e., discriminates) a polarization component of the modulated reference beam 38 for passage to the photorefractive sensing medium 40. Polarizer 88 may comprise a high extinction ratio polarizer of the type well known in the art and readily commercially available.

The sensing medium 40 may comprise a photorefractive substance, such as a bismuth silicon oxide crystal. As used herein, the term "photorefractive" refers to those materials wherein the space charge electrical grating can be either in-phase or out-of-phase with the optical interference pattern. When the modulated object and reference beams 34 and 38 are re-combined within the sensing medium 40, they create a space charge field (not shown) having a magnitude that is directly proportional to the vibrational displacement or amplitude of the traveling waves (e.g., traveling wave 16) in the paper sample 12. The magnitude of the space charge field is also related to a cosine function of the vibration phase of the traveling wave 16, at least for small amplitude displacements. The space charge field modulates the local refractive index of the sensing medium 40 by the electro-optical effect, creating a diffraction grating within the sensing medium 40 that embodies the desired low-frequency phase information. The result is the formation of a hologram (not shown) from which may be reconstructed an image 14 (illustrated generally in FIG. 2) of the traveling elastic wave. The intensity variations of the reconstructed image 14 are proportional to the phase difference between the modulated object and reference beams 34 and 38, respectively.

Since the modulated reference beam 38 has been modulated at a rate that is very close to but different than the frequency of the traveling wave 16, the features of the reconstructed image 14 will move at a speed that is related to the frequency difference between the modulated object beam 34 and the modulated reference beam 38. Since, as was mentioned above, the photorefractive material comprising the sensing medium 40 has an intrinsic response time (i.e., cut-off frequency), the offset or difference frequency between the modulated object and reference beams 34 and 38 must be below the cut-off frequency of the photorefractive material. If the difference frequency is too great, the resulting interference pattern will move so rapidly that the photorefractive material will fail to record the change.

The bismuth silicon oxide material which may comprise the photorefractive sensing medium 40 in one preferred embodiment has a high frequency cut-off of about 67 Hz. Alternatively, photorefractive sensing media having other high frequency cut-offs (e.g., high frequency cut-offs of about 1 kHz) are known and may be used as well. In any event, in order to detect traveling waves, the reference beam 26 should be modulated at a frequency so that the difference frequency between the modulated reference beam 38 and the modulated object beam 34 does not exceed the high frequency cut-off of the photorefractive sensing medium 40. In accordance with the foregoing considerations, then, the variable oscillator 76 in one preferred embodiment of the present invention is set to modulate the phase of the reference beam at a frequency that is about ±25 Hz from the frequency of the modulated object beam 34. For example, if it is desired to examine traveling waves having frequencies of about 40 kHz, then it will be desirable to modulate the phase of the reference beam 26 at a frequency of about 40 kHz±25 Hz. Similarly, if traveling waves having frequencies of about 100 kHz are to be examined, then the reference beam should be modulated at a frequency of about 100 kHz±125 Hz.

The reconstructed image 14 produced in the photorefractive sensing medium 40 may be observed by means of a suitable array (i.e., two-dimensional) detector 42, such as a CCD-type video camera 44. Alternatively, the reconstructed image 14 may by directly observed by the human eye via an eyepiece (not shown) or other such device. Generally speaking, for optically active materials such as BSO, it will be desirable to adjust the thickness of the sensing medium 40 in order to achieve a 90° polarization shift between the diffracted modulated reference beam 38 and the transmitted modulated object beam 34. Such a polarization shift enables the directly transmitted object beam 34 to be eliminated by a properly oriented polarizer 90 positioned between the detector 42 and photorefractive sensing medium 40. Finally, depending on the type of detector utilized, it may be necessary to position a focusing lens 92 between the detector 42 and the photorefractive sensing medium 40.

If a video camera 44 is used to detect the reconstructed image 14, the video camera 44 may be connected to a suitable display device 46, such as a CRT monitor or LCD panel, suitable for displaying the reconstructed image 14. Optionally, the image 14 captured by the video camera 44 may be recorded on a suitable medium (e.g., video tape) for later playback and/or analysis.

The apparatus 10 for assessing a material property of a sheet-like material (e.g., paper sample 12) may be operated according to the method 48 illustrated in FIG. 4. The first step 50 in the method 48 is to illuminate the paper sample 12 with the expanded object beam 30. The paper sample 12 may then be vibrated in step 52 to cause the formation of one or more traveling waves (e.g., traveling wave 16) in the paper sample 12. In an alternative arrangement, the paper sample 12 may be vibrated before illuminating the paper with the expanded object beam 30. That is, step 52 may be performed before step 50. In still another alternative arrangement, the illumination and vibrations steps 50 and 52 may be performed essentially simultaneously. Regardless of the particular arrangement, the traveling wave 16 produced in the paper sample 12 modulates the phase of the expanded object beam 30 to produce the modulated object beam 34. The next step in the method 40 is to modulate the reference beam 26 to produce a modulated reference beam 38. In the embodiment shown and described herein, the phase of the reference beam 26 is modulated at a frequency that is slightly different than the frequency of the traveling wave 16 that is to be imaged. The modulated object and reference beams 34 and 38 are then combined within the sensing medium 40 at step 56 to produce a hologram (not shown) from which may be reconstructed an image 14 (FIG. 2) of the traveling wave 16. The image 14 of the traveling wave 16 is then detected at step 58 and analyzed at step 60 to assess a material property of the sheet-like material (e.g. paper sample 12).

The traveling wave pattern contained in the reconstructed image 14 may be analyzed by measuring the wavelength of one wave at each of several different angular positions about the point of origin. The phase velocities of the waves may then be determined for specific directions in the paper sample by multiplying the measured wavelengths by the excitation frequency. Hence, anisotropic stiffness properties in the paper sample can be characterized and correlated. For example, the traveling wave pattern 14 illustrated in FIG. 2 is generally oblong, with a "major axis" 94 being slightly inclined from a vertical axis 96. The traveling wave 16 travels at the greatest velocity in a direction that extends along the major axis 94. Therefore, the stiffness of the paper sample 12 represented in FIG. 2 is not the same in every direction. Instead, the paper sample 12 is anisotropic, with the stiffness of the paper being generally greatest in the direction corresponding to the major axis 94 of the oblong traveling wave pattern.

In the embodiment shown and described herein, it is generally preferred, but not required, to transform the traveling wave image data represented in the reconstructed image 14 from the spatial domain into the spatial frequency domain, such as, for example, by means of a Fourier transform. Such transformed traveling wave image data 74 is illustrated generally in FIG. 4. The Fourier transform of a single outward traveling wave (e.g., wave 16) is a single ring which shows explicitly the wavelength anisotropy in all directions along the paper sample 12 simultaneously. For example, in the sample illustrated herein, the Fourier transform of the generally oblong traveling wave 16 shown in FIG. 2 is a generally oblong ring 98 having a "minor axis" 95 that is also inclined with respect to a vertical axis 97. From such data, the wave speeds in all directions, elastic constants, and anisotropy may be determined.

If such a Fourier transform is to be utilized, then it may be desirable to connect the detector 42 (e.g., video camera 44) to a computer (not shown) capable of performing a Fourier transform of the video image data. For example, in one preferred embodiment, such a computer (not shown) may be provided with a program for performing a fast Fourier transform (FFT) of the video image data. The transformed image data may then be presented for the user on a suitable display device (e.g., a CRT monitor or LCD panel) associated with the computer. Alternatively, the Fourier transform could be performed totally optically without the aid of a computer. However, since computers, computer programs, and optical transform techniques for performing such FFT conversions are well-known in the art and readily commercially available, the particular computer system or optical transform system that may be utilized in one preferred embodiment of the invention will not be described in further detail herein.

As described herein, it is generally preferred, but not required, to utilize the present invention to detect and monitor traveling waves of the zeroth order anti-symmetric (i.e., $A_0$) mode. Such zeroth order anti-symmetric mode traveling waves, while having larger amplitudes than zeroth order symmetric (i.e., $S_0$) mode waves, generally travel at slower velocities than $S_0$ mode waves. Consequently, it is generally preferred, but not required, to use the following type of analysis in order to determine the elastic properties of the paper sample 12 based on the detection and analysis of an $A_0$ mode traveling wave.

In most paper processing applications, it is generally desirable to determine the elastic properties (e.g., stiffness) of the paper sample 12 in both the machine direction (MD) and the cross direction (CD). These directions are generally perpendicular to one another. Since, in the past, the symmetric $S_0$ wave mode was measured, the paper industry has compiled a substantial database of information that relates the ratio of $S_0$ traveling wave velocities in the machine and cross directions (i.e., the MD/CD velocity ratio) to the elastic properties of paper. However, this ratio is not the same for anti-symmetric traveling waves. That is, merely calculating the MD/CD ratio for anti-symmetric traveling waves will not produce an accurate correlation in the existing database. However, the square of the MD/CD ratio for anti-symmetric traveling waves does produce an accurate correlation. Put in other words, the square of the MD/CD velocity ratio for traveling waves of the anti-symmetric mode at low frequencies yields substantially the same information about the elastic properties of the paper sample as does the plain MD/CD ratio for traveling waves of the symmetric mode. Therefore, the existing database may be used to derive information about the material properties of the paper sample by merely utilizing the square of the MD/CD velocity ratio for anti-symmetric waves.

This completes the detailed description of the various embodiments of the method and apparatus according to the present invention. While a number of specific components were described above for the preferred embodiments of this invention, persons having ordinary skill in the art will readily recognize that other substitute components or combinations of components may be available now or in the future to accomplish comparable functions to the various components shown and described herein. For example, while the sensing medium 40 may comprise a bismuth silicon oxide crystal, other materials that are now known in the art or that may be developed in the future may be used to form a hologram from which may be reconstructed an image of the traveling waves contained on the vibrating paper sample 12. Also, while the excitation source 18 may comprise a laser 20 for directing a beam 62 onto the front surface of the paper sample 12, the beam could also be directed to the opposite surface (i.e., the back surface) of the paper sample 12, or simultaneously to both sides of the paper. As mentioned above, the energy delivered by the beam 62 may be sufficient to induce vibrations in the paper sample 12 by either thermoelastic expansion or by ablation. Continuous excitation sources could also be used to induce the required vibrations in the paper sample 12 as was mentioned herein.

Accordingly, it should be understood that the inventive concepts herein described may be variously otherwise embodied and it is intended that the appended claims be construed to include alternative embodiments of the invention except insofar as limited by the prior art.

We claim:

1. A method for assessing a material property of a sheet-like material, comprising:

vibrating the sheet-like material to produce at least one traveling wave therein;

directing an object wavefront toward the vibrating sheet-like material so that said object wavefront is modulated by the vibrating sheet-like material to produce a modulated object wavefront;

modulating a reference wavefront in synchronization with the vibrating sheet-like material to produce a modulated reference wavefront so that a difference frequency between the modulated object wavefront and the modulated reference wavefront is within the response range of a sensing medium;

combining the modulated object wavefront and the modulated reference wavefront within the sensing medium to produce an output beam that contains an image of the traveling wave in the sheet-like material, the image of the traveling wave being related to a displacement amplitude of the traveling wave over a two-dimensional area of the vibrating sheet-like material;

detecting an image of the traveling wave in the vibrating sheet-like material; and assessing the material property of the vibrating sheet-like material based on the detected image of the traveling wave.

2. The method of claim 1, wherein the step of vibrating the sheet-like material comprises the step of vibrating the sheet-like material at an ultrasonic frequency.

3. The method of claim 1, wherein the sheet-like material is vibrated in an intermittent manner by thermo-elastic expansion.

4. The method of claim 1, wherein the sheet-like material is vibrated in an intermittent manner by thermal ablation.

5. The method of claim 1, wherein the step of assessing the material property of the sheet-like material includes the step of assessing material stiffness in at least two directions simultaneously.

6. The method of claim 5, wherein the traveling wave comprises an anti-symmetric mode traveling wave.

7. The method of claim 6, wherein the step of assessing material stiffness in at least two directions comprises the steps of:

determining a velocity of the anti-symmetric traveling wave in a first direction;

determining a velocity of the anti-symmetric wave in a second direction; and mathematically analyzing the velocities of the anti-symmetric traveling waves in the first and second directions to produce a characterization of the material stiffness.

8. The method of claim 7, wherein the step of mathematically analyzing the velocities comprises the step of squaring a ratio of the velocity of the anti-symmetric wave in the first direction and the velocity of the anti-symmetric wave in the second direction.

9. The method of claim 7, wherein the first direction comprises a machine direction and wherein the second direction comprises a cross direction.

10. Apparatus for producing an indication of a material property of a sheet-like material comprising:

an excitation source for vibrating the sheet-like material to produce at least one traveling wave therein;

a light source configured to produce an object wavefront and a reference wavefront, said light source directing the object wavefront toward the sheet-like material to produce a modulated object wavefront;

a modulator operatively associated with the reference wavefront, said modulator modulating the reference wavefront in synchronization with the traveling wave on the sheet-like material to produce a modulated reference wavefront;

a sensing medium positioned to receive the modulated object wavefront and the modulated reference wavefront, the sensing medium having a response range, the modulated reference wavefront being modulated by said modulator so that a difference frequency between the modulated object wavefront and the modulated reference wavefront is within the response range of said sensing medium, the modulated object wavefront and the modulated reference wavefront combining in said sensing medium to produce an output beam that contains an image of the traveling wave in said sheet-like material, the image of the traveling wave being related to a displacement amplitude of the traveling wave over a two-dimensional area of the vibrating sheet-like material; and a detector configured to detect the image of the traveling wave in said sheet-like material.

11. The apparatus of claim 10, wherein said traveling wave comprises an anti-symmetric mode traveling wave.

12. The apparatus of claim 10, wherein said excitation source comprises a laser.

13. The apparatus of claim 12, wherein said laser produces a pulsed beam that vibrates the sheet-like material in an intermittent manner due to thermo-elastic expansion.

14. The apparatus of claim 12, wherein said laser produces a pulsed beam that vibrates the sheet-like material in an intermittent manner due to thermal ablation.

15. The apparatus of claim 10, wherein said light source comprises a laser.

16. The apparatus of claim 10, wherein said sensing medium comprises a photorefractive material, the modulated object wavefront and the modulated reference wavefront interfering with one another within said photorefractive material to generate a space charge field within the photorefractive material.

17. The apparatus of claim 10, wherein said object wavefront comprises an object beam of coherent light and wherein said reference wavefront comprises a reference beam of coherent light.

18. The apparatus of claim 10, wherein said modulator comprises a phase modulator for modulating a phase of said reference wavefront.

19. The apparatus of claim 10, wherein said detector comprises a camera.

20. The apparatus of claim 10, wherein said light source comprises abeam splitter for producing the object wavefront and the reference wavefront from a single wavefront.

21. A method for assessing a material property of a sheet-like material, comprising:

providing a sensing medium, said sensing medium having a response range;

producing an object wavefront and a reference wavefront;

vibrating the sheet-like material to produce at least one traveling wave therein;

directing the object wavefront toward the vibrating sheet-like material so that said object wavefront is modulated by the vibrating sheet-like material to produce a modulated object wavefront;

modulating the reference wavefront in synchronization with the vibrating sheet-like material to produce a modulated reference wavefront so that a difference frequency between the modulated object wavefront and the modulated reference wavefront is within the response range of the sensing medium;

combining the modulated object wavefront and the modulated reference wavefront within the sensing medium to produce an output beam that contains an image of the traveling wave in the vibrating sheet-like material, the image of the traveling wave being related to a displacement amplitude of the traveling wave over a two-dimensional area of the vibrating sheet-like material;

detecting an image of the traveling wave in the vibrating sheet-like material; and assessing the material property of the vibrating sheet-like material based on the detected image of the traveling wave.

22. The method of claim 21, wherein the step of vibrating the sheet-like material comprises the step of vibrating the sheet-like material at an ultrasonic frequency.

23. The method of claim 21, wherein the sheet-like material is vibrated in an intermittent manner.

24. The method of claim 23, wherein the sheet-like material is vibrated in an intermittent manner by thermoelastic expansion.

25. The method of claim 23, wherein the sheet-like material is vibrated in an intermittent manner by thermal ablation.

26. The method of claim 21, wherein the step of assessing the material property of the sheet-like material includes the step of assessing material stiffness in at least two directions simultaneously.

27. The method of claim 26, wherein the traveling wave comprises an anti-symmetric mode traveling wave.

28. The method of claim 27, wherein the step of assessing material stiffness in at least two directions comprises the steps of:

determining a velocity of the anti-symmetric wave in a first direction;

determining a velocity of the anti-symmetric wave in a second direction; and mathematically analyzing the velocities of the anti-symmetric traveling waves in the first and second directions to produce a characterization of the material stiffness.

29. The method of claim 28, wherein the step of mathematically analyzing the velocities comprises squaring a ratio of the velocity of the anti-symmetric wave in the first direction and the velocity of the anti-symmetric wave in the second direction.

30. The method of claim 28, wherein the first direction comprises a machine direction and wherein the second direction comprises a cross direction.

* * * * *